United States Patent

Hasegawa et al.

Patent Number: 4,606,857
Date of Patent: Aug. 19, 1986

[54] MURAMYLDIPEPTIDE DERIVATIVES

[75] Inventors: Akira Hasegawa, Gifu; Ichiro Azuma, Hokkaido; Yuichi Yamamura, Hyogo, all of Japan

[73] Assignee: Daiichi Seiyaku Co., Ltd., Tokyo, Japan

[21] Appl. No.: 517,551

[22] Filed: Jul. 27, 1983

[30] Foreign Application Priority Data

Jul. 27, 1982 [JP] Japan .................... 57-130705

[51] Int. Cl.$^4$ .............................. C07K 9/00
[52] U.S. Cl. .................................. 260/998.2
[58] Field of Search ........................ 260/112.5 R

[56] References Cited

U.S. PATENT DOCUMENTS

| 4,082,736 | 4/1978 | Jones et al. | 260/112.5 R |
| 4,094,971 | 6/1978 | Chedid et al. | 260/112.5 R |
| 4,101,536 | 7/1978 | Yamamura et al. | 260/112.5 R |
| 4,101,649 | 7/1978 | Adam nee Chosson et al. | 260/112.5 R |
| 4,153,684 | 5/1979 | Audibert et al. | 260/112.5 R |
| 4,272,524 | 6/1981 | Chedid et al. | 260/112.5 R |
| 4,314,998 | 2/1982 | Yamamura et al. | 260/112.5 R |
| 4,317,771 | 3/1982 | Shiba et al. | 260/112.5 R |
| 4,357,322 | 11/1982 | Rooks, II et al. | 260/112.5 R |
| 4,423,038 | 12/1983 | Baschang et al. | 260/112.5 R |

OTHER PUBLICATIONS

Carbohydr. Res. 108(1), 139–47.
Chem. Abstr., vol. 100, (1984) 175252u.
Chem. Abstr., vol. 97, (1982) 174449w.
Chem. Abstr., vol. 101, (1984) 38830n.
Chem. Abstr., vol. 99, (1983) 88560k.

Primary Examiner—Delbert R. Phillips
Attorney, Agent, or Firm—Sughrue, Mion, Zinn, Macpeak, and Seas

[57] ABSTRACT

Muramyldipeptide derivatives represented by the formula:

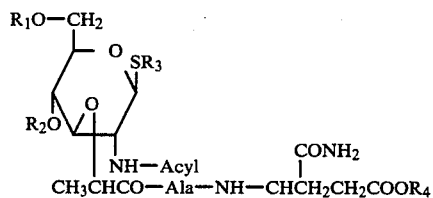

wherein Ala represents alanine; Acyl represents an acyl group; $R_1$ and $R_2$ each represents a hydrogen atom or, when taken together, may form an alkylidene group; $R_3$ represents a hydrogen atom, an acyl group or an alkyl group; and $R_4$ represents a hydrogen atom or an alkyl group. These compounds have excellent immunoadjuvant activity, prophylactic and therapeutic effects against microbial infections, and antitumor activity.

9 Claims, No Drawings

MURAMYLDIPEPTIDE DERIVATIVES

FIELD OF THE INVENTION

This invention relates to novel muramyldipeptide derivatives having excellent immunoadjuvant activity and prophylactic and therapeutic effects against microbial infections and antitumor activity and, more specifically, this invention relates to a muramyldipeptide derivative represented by the formula (I):

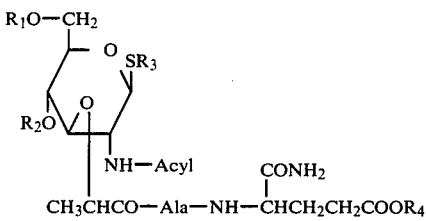

wherein Ala represents alanine; Acyl represents an acyl group having 2 to 40 carbon atoms; $R_1$ and $R_2$ each represents a hydrogen atom, or $R_1$ and $R_2$, when taken together, may form an alkylidene group having 1 to 6 carbon atoms; $R_3$ represents a hydrogen atom, an acyl group having 2 to 40 carbon atoms or an alkyl group having 1 to 40 carbon atoms; and $R_4$ represents a hydrogen atom or an alkyl group having 1 to 20 carbon atoms.

BACKGROUND OF THE INVENTION

Hitherto, certain types of muramyldipeptide derivatives have been known to have useful immunotherapeutic activities. For example, U.S. Pat. No. 4,101,536 discloses muramyldipeptide derivatives and the salts thereof having potent immunoadjuvant activity and antitumor activity and being applicable as an agent for the immunotherapy of cancer for human and animals. These known compounds, however, have a free hydroxy group at the 1-position of muramic acid of N-acetylmuramyldipeptide and do not possess an S-substituted moiety at the 1-position.

SUMMARY OF THE INVENTION

As a result of extensive studies on compounds useful as adjuvant substances, we have found that the compounds of the above formula (I) which are obtained by introducing a sulfur atom to the 1-position of muramic acid of N-acylmuramyldipeptides, the minimum unit constituting bacterial cell wall of human type *Mycobacterium tuberculosis,* BCG and other mycobacteria as well as cellular parastic bacteria, have excellent immunoadjuvant activity, and thus completed the present invention.

The compounds according to the present invention are of low toxicity and possess excellent immunoadjuvant activity and, therefore, can be useful for various diseases attributed to reduction in immunity function, for example, as prophylactic and therapeutic agents against microbial infections, antitumor agents and the like.

DETAILED DESCRIPTION OF THE INVENTION

The muramyldipeptide derivatives of the present invention are represented by the formula (I)

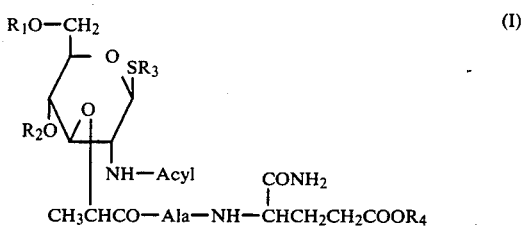

wherein Ala represents alanine; Acyl represents an acyl group having 2 to 40 carbon atoms; $R_1$ and $R_2$ each represents a hydrogen atom, or $R_1$ and $R_2$, when taken together, may form an alkylidene group having 1 to 6 carbon atoms; $R_3$ represents a hydrogen atom, an acyl group having 2 to 40 carbon atoms or an alkyl group having 1 to 40 carbon atoms; and $R_4$ represents a hydrogen atom or an alkyl group having 1 to 20 carbon atoms.

A preferred class of compounds according to the present invention is that having the formula (I) above wherein $R_1$ and $R_2$ each represents a hydrogen atom; $R_3$ represents an acyl group having 2 to 40 carbon atoms; and $R_4$ represents an alkyl group having 1 to 20 carbon atoms.

Particularly preferred compounds of the present invention are 2-acetamido-2-deoxy-1-S-decanoyl-3-O-(D-2-propanoyl-L-alanyl-D-isoglutamine methyl ester)-1-thio-β-D-glucopyranose, 2-acetamido-1-S-acetyl-2-deoxy-3-O-(D-2-propanyl-L-alanyl-D-isoglutamine methyl ester)-1-thio-β-D-glucopyranose, 2-acetamido-2-deoxy-3-O-(D-2-propanoyl-L-alanyl-D-isoglutamine methyl ester)-1-thio-β-D-glucopyranose, 2-acetamido-2-deoxy-3-O-(D-2-propanoyl-L-alanyl-D-isoglutamine)-1-thio-β-D-glucopyranose, 2-acetamido-2-deoxy-1-S-hexadecanoyl-3-O-(D-2-propanoyl-L-alanyl-D-isoglutamine methyl ester)-1-thio-β-D-glucopyranose, 2-acetamido-2-deoxy-1-S-hexadecanoyl-3-O-(D-2-propanoyl-L-alanyl-D-isoglutamine)-1-thio-β-D-glucopyranose, and 2-acetamido-2-deoxy-1-S-eicosanoyl-3-O-(D-2-propanoyl-L-alanyl-D-isoglutamine)-1-thio-β-D-glucopyranose.

The effects of the compounds of the present invention were confirmed by the following method.

(1) Adjuvant Activity

The adjuvant activity was confirmed by the enhancing activity on the induction of delayed-type hypersensitivity to N-acetyltyrosine-3-azobenzene-4'-arsonic acid (hereinafter referred to as ABA-N-Ac-Tyr) in guinea pig.

That is, a water-in-oil emulsion prepared by mixing 50 μg/animal of ABA-N-Ac-Tyr and 100 μg/animal of each of the compounds of the present invention with Freund's incomplete adjuvant (hereinafter referred to as FIA) was administered to the soles of guinea pigs. Two weeks later, 100 μg of 3-azobenzene-4'-arsonic acid bonded to bovine serum albumin (hereinafter referred to as ABA-BSA) was intradermally injected and the diameter of skin reaction (i.e., erythema and induration) was measured 24 hours and 48 hours after the injection. The diameter of the skin reaction is considered a measure of cellular immunity. The results obtained are shown in Table 1 below.

TABLE 1

Adjuvant Activity on Induction of Delayed-Type Hypersensitivity

| Compound No.* | Dose (μg) | Skin Reaction 24 Hours (mm ± SE) | 48 Hours (mm ± SE) |
|---|---|---|---|
| 2 | 100 | 21.0 ± 1.0 | 21.0 ± 0.7 |
| 3 | 100 | 22.1 ± 0.9 | 20.9 ± 0.7 |
| 4 | 100 | 23.1 ± 1.2 | 21.0 ± 1.3 |
| 8 | 100 | 14.5 ± 0.7 | 10.3 ± 1.0 |
| 9 | 100 | 13.5 ± 0.8 | 12.4 ± 0.7 |
| 10 | 100 | 17.4 ± 1.7 | 13.6 ± 1.8 |
| 11 | 100 | 15.6 ± 1.9 | 11.6 ± 1.4 |
| 14 | 100 | 20.4 ± 0.7 | 21.0 ± 1.4 |
| 15 | 100 | 16.9 ± 0.8 | 14.0 ± 1.0 |
| 16 | 100 | 11.3 ± 0.8 | 5.6 ± 1.4 |
| 17 | 100 | 21.8 ± 0.8 | 23.1 ± 1.1 |
| Control (ABA—Tyr+FIA) | | 4.5 ± 0.3 | 2.9 ± 0.7 |

(2) Prophylactic Effect Against Microbial Infection

Animals: Groups of 20 STD-ddy male mice, 5 weeks of age, were used.

Bacteria: *E. coli* E77156 which has been maintained in a freezed-culture was used.

Agents: Compounds of the present invention were dissolved or suspended in Dulbecco phosphate-buffered saline (PBS: pH 7.4) at a concentration of 500 μg/ml just before use.

Treatment and Infection: The animals were treated subcutaneously with 0.2 ml of each of the above solution or suspension (equivalent to 100 μg/mouse), followed by the subcutaneous challenge with *E. coli* 24 hours later.

The effect was judged from the percent survival of the mice seven days after the infection. As is apparent from the results shown in Table 2 below, the compounds of the present invention exhibit excellent prophylactic effect against microbial infection.

TABLE 2

Prophylactic Effect in Mice Infected with *E. coli* E 77156

| Compound No. | Number of Mice Used | % Survival 7 days after Infection Inoculum Size (cells/mouse) *E. coli* E 77156 | | |
|---|---|---|---|---|
| | | 4.4 × 10⁶ | 6.17 × 10⁶ | 6.88 × 10⁶ |
| 4 | 20 | 55 | | |
| 14 | 20 | 80 | | |
| 17 | 20 | 60 | | |
| 18 | 20 | | 90 | |
| 19 | 20 | | 70 | |
| 21 | 20 | | 50 | |
| 22 | 20 | | 55 | |
| 23 | 20 | | 60 | |
| 24 | 20 | | 65 | |
| 25 | 20 | | | 55 |
| PBS control | 20 | 5 | 5 | 5 |

(3) Antitumor Activity Against Meth-A System

A mixture of tumor cells (Meth-A, 1.5×10⁶) and 100 μg of Compound 20 of the present invention suspended in PBS was inoculated intradermally in BALB/c mice. Suppression of Meth-A growth in BALB/c on the 27th day after inoculation was found to be 5/9. The value is expressed in terms of the number of tumor-free mice/the number of mice tested.

The test compounds used in the above experiments (1), (2) and (3) are as follows.

Compound 2: 2-Acetamido-1-S-acetyl-2-deoxy-3-O-(D-2-propanoyl-L-alanyl-D-isoglutamine methyl ester)-1-thio-β-D-glucopyranose Compound 3: 2-Acetamido-2-deoxy-3-O-(D-2-propanoyl-L-alanyl-D-isoglutamine methyl ester)-1-thio-β-D-glucopyranose Compound 4: 2-Acetamido-2-deoxy-3-O-(D-2-propanoyl-L-aranyl-D-isoglutamine)-1-thio-β-D-glucopyranose Compound 8: 1-S-n-Butyl 2-acetamido-2-deoxy-3-O-(D-2-propanoyl-L-alanyl-D-isoglutamine methyl ester)-1-thio-β-D-glucopyranoside Compound 9: 1-S-Hexadecanyl 2-acetamido-2-deoxy-3-O-(D-2-propanoyl-L-alanyl-D-isoglutamine methyl ester)-1-thio-β-D-glucopyranoside Compound 10: 1-S-n-Butyl 2-acetamido-2-deoxy-3-O-(D-2-propanoyl-L-alanyl-D-isoglutamine)-1-thio-β-D-glucopyranoside Compound 11: 1-S-Hexadecanyl 2-acetamido-2-deoxy-3-O-(D-2-propanoyl-L-alanyl-D-isoglutamine)-1-thio-β-D-glucopyranoside Compound 14: 2-Acetamido-2-deoxy-1-S-hexadecanoyl-3-O-(D-2-propanoyl-L-alanyl-D-isoglutamine methyl ester)-1-thio-β-D-glucopyranose Compound 15: 2-Acetamido-2-deoxy-4,6-O-isopropylidene-3-O-(D-2-propanoyl-L-alanyl-D-isoglutamine)-1-thio-β-D-glucopyranose Compound 16: 2-Acetamido-2-deoxy-1-S-hexadecanoyl-4,6-O-isopropylidene-3-O-(D-2-propanoyl-L-alanyl-D-isoglutamine)-1-thio-β-D-glucopyranose Compound 17: 2-Acetamido-2-deoxy-1-S-hexadecanoyl-3-O-(D-2-propanoyl-L-alanyl-D-isoglutamine)-1-thio-β-D-glucopyranose Compound 18: 2-Acetamido-2-deoxy-1-S-decanoyl-3-O-(D-2-propanoyl-L-alanyl-D-isoglutamine methyl ester)-1-thio-β-D-glucopyranose Compound 19: 2-Acetamido-2-deoxy-1-S-octadecanoyl-3-O-(D-2-propanoyl-L-alanyl-D-isoglutamine methyl ester)-1-thio-β-D-glucopyranose Compound 20: 2-Acetamido-2-deoxy-1-S-triacontanoyl-3-O-(D-2-propanoyl-L-alanyl-D-isoglutamine methyl ester)-1-thio-β-D-glucopyranose Compound 21: 2-Acetamido-2-deoxy-1-S-n-butanoyl-3-O-(D-2-propanoyl-L-alanyl-D-isoglutamine methyl ester)-1-thio-β-D-glucopyranose Compound 22: 2-Acetamido-2-deoxy-1-S-dodecanoyl-3-O-(D-2-propanoyl-L-alanyl-D-isoglutamine)-1-thio-β-D-glucopyranose.

Compound 23: 2-Acetamido-2-deoxy-1-S-tetradecanoyl-3-O-(D-2-propanoyl-L-alanyl-D-isoglutamine)-1-thio-β-D-glucopyranose Compound 24: 2-Acetamido-2-deoxy-1-S-tetradecanoyl-3-O-(D-2-propanoyl-L-alanyl-D-isoglutamine methyl ester)-1-thio-β-D-glucopyranose.

Compound 25: 2-Acetamido-2-deoxy-1-S-eicosanoyl-3-O-(D-2-propanoyl-L-alanyl-D-isoglutamine)-1-thio-β-D-glucopyranose.

The compounds of the present invention can be prepared according to the following reaction scheme.

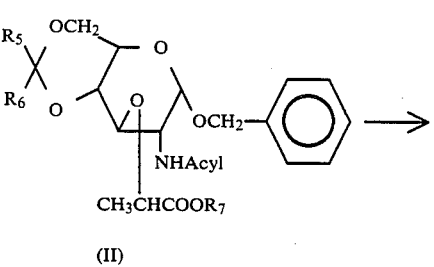

(II)

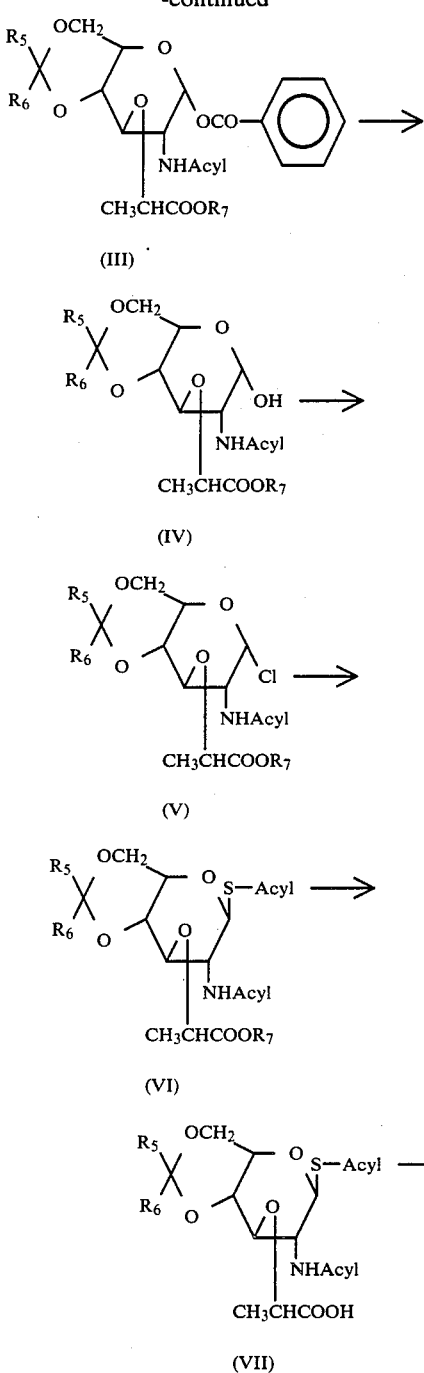

In the above reaction scheme, $R_5$ represents a hydrogen atom or an alkyl group having 1 to 6 carbon atom, and $R_6$ and $R_7$ each represents an alkyl group having 1 to 6 carbon atom.

That is, the compound (II) is oxidized in the presence of a solvent, such as dichloromethane, using a chromic anhydride-pyridine complex at a temperature of about 0° C. to 60° C. to obtain the compound (III). The compound (III) is reacted with a metal alcoholate in an alcohol solvent to obtain the compound (IV). The compound (IV) is dissolved in a solvent, such as a mixed solvent of dichloromethane and carbon tetrachloride, and then reacted with hexamethylphosphorus triamide [P(NMe$_2$)$_3$] at a low temperature, preferably −40° C. or lower, to obtain the compound (V). The compound (V) is dissolved in a solvent or a mixture of solvents, for example, a mixture of dichloromethane and acetone, and reacted with an alkali thio-organic acid, for example, potassium thioacetate (CH$_3$COSK), to obtain the compound (VI). The compound (VI) is reacted with an alkali hydroxide in the presence of a solvent, such as dioxane, to hydrolyze the S-acetyl group and alkoxycarbonyl group and then the hydrolysate is reacted with an organic acid anhydride such as acetic anhydride, and triethylamine to acylate the SH group thereby obtaining the compound (VII).

The compound (VII) thus obtained is then condensed with an alanyl-isoglutamine alkyl ester to obtain the desired compound of the formula (I) wherein $R_1$ and $R_2$ are bonded together to form an alkylidene group; $R_3$ is an acyl group; and $R_4$ is an alkyl group.

The above condensation reaction can be carried out by methods commonly employed for peptide syntheses, i.e., carbodiimide method, eintops method, active ester method, acid anhydride method and the like. For example, the compound (VII) is dissolved in a solvent such as dioxane, and dicyclohexylcarbodiimide and N-hydroxysuccinic acid imide or 1-hydroxybenzotriazole are added to the solution at about 0° C. to 60° C. to form an active ester of the compound (VII). To the resulting reaction mixture is added an L-alanyl-D-isoglutamine alkyl ester at about 0° C. to 60° C. to obtain the above-described compound (I).

The S-acyl group of the compound (I) thus obtained can be converted into a free SH group by reacting the compound (I) with a metal alcoholate in an alcoholic solution at about 0° C. to room temperature, followed by neutralization with a cation exchange resin, etc. The thus obtained SH-compound may be converted into an S-acylated compound by reacting with an acyl halide in a solvent, such as dichloromethane, in the presence of an acid acceptor such as pyridine, at about −10° C. to 50° C. Further, the S-alkylated compound can be obtained by reacting the above S-acylated compound with a sodium alcoholate in an alcohol and, without conducting neutralization, the resulting product is then reacted with an alkyl halide at 0° to 40° C. The alkylidene group can be released by reacting with a 50–90% aqueous solution of acetic acid at room temperature to 100° C. The conversion of the alkoxycarbonyl group to a carboxyl group can be accomplished by reacting with an aqueous alkali hydroxide solution in an alcoholic solution at 0° to room temperature and then neutralizing with a cation exchange resin, etc.

The present invention will now be described in greater detail with reference to examples but the scope of the invention is not limited thereto. Unless otherwise indicated, a mixture of solvents is by volume.

EXAMPLE 1

(1) 164.7 mg of chromic anhydride and 0.25 ml of pyridine were added to 5 ml of dichloromethane and the mixture was stirred for 15 minutes. To the resulting mixture were added 180 mg of benzyl 2-acetamido-2-deoxy-4,6-O-isopropylidine-3-O-[D-1-(methoxycarbonyl)ethyl]-α-D-glucopyranoside (compound II) dissolved in 3 ml of dichloromethane and then 0.16 ml of acetic anhydride.

The reaction mixture was stirred at 45° C. for 3 hours and passed through a column of silica gel (Wako-C-200, 20 g), and the column was eluted with ethyl acetate to obtain 170 mg (yield: 92%) of 2-acetamido-1-o-benzoyl-2-deoxy-4,6-O-isopropylidene-3-O-[D-1-(methoxycarbonyl)ethyl]-α-D-glucopyranose (compound III) having a melting point of 134°–137° C.

$[\alpha]_D^{25} +144°$ (c=1.5, methanol).

Elemental Analysis for $C_{22}H_{29}NO_9$: Calcd. (%): C, 58.53; H, 6.47; N, 3.10; Found (%): C, 58.39; H, 6.58; N, 3.02.

(2) To a solution of 4.0 g of the compound (III) in 60 ml of absolute methanol, about 30 mg of metal sodium was added under cooling. After allowing to stand at room temperature for 10 minutes, the mixture was treated with Amberlite IRC-50. The solution was concentrated and the resulting syrup was purified by column chromatography using silica gel (50 g) (developing agent (a): chloroform, developing agent (b): chloroform-methanol=50:1). From the effluent (b), there was obtained 2.8 g (yield: 93%) of 2-acetamido-2-deoxy-4,6-O-isopropylidene-3-O-[D-1-(methoxycarbonyl)ethyl]-D-glucopyranose (compound IV) having a melting point of 180°–184° C.

$[\alpha]_D^{25} +44.3°$ (c=0.47, chloroform, equilibrium).

Elemental Analysis for $C_{15}H_{25}NO_8$: Calcd. (%): C, 51.86; H, 7.25; N, 4.03; Found (%): C, 51.81; H, 7.29; N, 3.96.

(3) 2.5 g of the compound (IV) was dissolved in a mixture of 50 ml of anhydrous dichloromethane and 2.17 g of anhydrous carbon tetrachloride and the mixture was cooled to −50° C. To the resulting mixture was added a solution of 1.6 g of hexamethylphosphorus triamide in 25 ml of anhydrous dichloromethane over 15 minutes while stirring at −50° C., and the reaction was conducted for 1 hour. The reaction mixture was concentrated under reduced pressure (bath temperature: 40° C.). At this stage, the thin layer chromatography revealed the presence of a mixture of α- and β-chlorides and oxazoline. By repeating the above procedure of addition of anhydrous dichloromethane followed by concentration three to four times, all the chlorides were led to the α-chloro derivative. The α-chloride was dissolved in a mixed solution of 15 ml of anhydrous dichloromethane and 15 ml of anhydrous acetone, and 2.4 g of potassium thioacetate was added thereto, followed by stirring the mixture at room temperature overnight. After it was confirmed that all the chloride disappeared by thin layer chromatography, the reaction mixture was concentrated under reduced pressure, and the residue was extracted with chloroform, washed with water, and dried over sodium sulfate. The solvent was removed, and the residue was crystallized from diethyl ether to obtain 1.94 g (yield: 66.4%) of 2-acetamido-1-S-acetyl-2-deoxy-4,6-O-isopropylidene-3-O-[D-1-(methoxycarbonyl)ethyl]-1-thio-α-D-glucopyranose (compound VI) as a needle-like crystal. The filtrate was purified by silica gel (30 g) column chromatography (developing agent (a): chloroform; (b): chloroform-methanol=150:1). From the effluent (b) was obtained 500 mg (yield: 17.1%) of the compound (VI). Total yield: 2.44 g (83.5%); melting point: 171°–173° C.

$[\alpha]_D^{25} +8.1°$ (c=0.4, chloroform).

Elemental Analysis for $C_{17}H_{27}NO_8S$: Calcd. (%): C, 50.36; H, 6.71; N, 3.45; Found (%): C, 50.28; H, 6.59; N, 3.45.

(4) 200 mg of the compound (VI) was dissolved in 10 ml of 1,4-dioxane, and 12 ml of 0.2M potassium hydroxide was added thereto. After allowing the mixture to stand at room temperature for 10 minutes, the mixture was treated with Amberlite IRC-50 to remove the base. The resin was separated by filtration and washed with methanol. The filtrate and the washing were combined and concentrated under reduced pressure. The resulting syrup was dissolved in methanol, and 1 ml of triethylamine and 0.8 ml of anhydrous acetic acid were added to the solution under cooling, followed by reacting at room temperature for 30 minutes. The reaction mixture was concentrated under reduced pressure, and the resulting syrup was purified by silica gel (20 g) column chromatography (developing agent (a): chloroform; (b): chloroform-methanol=50:1). From the effluent (b), there was obtained 150 mg (yield: 78%) of 2-acetamido-1-S-acetyl-3-O-(D-1-carboxyethyl)-2-deoxy-4,6-O-isopropylidene-1-thio-α-D-glucopyranose (compound VII) as needle-like crystals. Recrystallization from diethyl ether gave a product having a melting point of 193°–200° C. (decomposition).

$[\alpha]_D^{25} +10.5°$ (c=0.3, chloroform).

Elemental Analysis for $C_{16}H_{25}NO_8S$: Calcd. (%): C, 49.09; H, 6.44; N, 3.58; Found (%): C, 49.13; H, 6.51; N, 3.48.

(5) 160 mg of the compound (VII) was dissolved in 5 ml of anhydrous 1,4-dioxane, and 210 mg of dicyclohexylcarbodiimide and 100 mg of N-hydroxysuccinimide were added to the solution, and the mixture was stirred at room temperature for 30 minutes. The diphenylurea formed was separated by filtration and washed with 2 ml of dioxane. The filtrate and the washing were combined, and 200 mg of L-alanyl-D-isoglutamine methyl ester trifluoroacetate and 5 drops of triethylamine were added thereto while stirring to effect a reaction at room temperature for 40 minutes. After completion of the reaction was confirmed by thin layer chromatography, the reaction mixture was concentrated under reduced pressure, and the resulting syrup was purified by silica gel (20 g) column chromatography (developing agent (a): chloroform; (b): chloroform-methanol=100:1; (c): chloroform-methanol=50:1). From the effluent (c), there was obtained 235 mg (yield: 95%) of the desired compounds, 2-acetamido-1-S-acetyl-2-deoxy-4,6-O-isopropylidene-3-O-(D-2-propanoyl-L-alanyl-D-isoglutamine methyl ester)-1-thio-β-D-glucopyranose (compound I). Recrystallization from diethyl ether gave a product having a melting point of 148°–151° C.

$[\alpha]_D^{25} +11°$ (c=0.2, chloroform).

Elemental Analysis for $C_{25}H_{40}N_4O_{11}S$: Calcd. (%): C, 49.66; H, 6.67; N, 9.27; Found (%): C, 49.76; H, 6.65; N, 9.30.

(6) 100 mg of the compound (I) was dissolved in 5 ml of a 80% aqueous acetic acid solution and heated at 45° C. for 45 minutes while stirring. The reaction mixture was concentrated under reduced pressure at below 40° C. The acetic acid was completely removed as an azeotropic mixture with toluene to obtain 2-acetamido-1-S-acetyl-2-deoxy-3-O-(D-2-propanoyl-L-alanyl-D-isoglutamine methyl ester)-1-thio-β-D-glucopyranose (Compound 2) that showed a single spot on the thin layer chromatogram. Recrystallization from diethyl ether gave a pure product having a melting point of 158°–162° C.

$[\alpha]_D^{25} +62°$ (c=0.2, chloroform-methanol=1:1).

Elemental Analysis for $C_{22}H_{36}N_4O_{11}S$: Calcd. (%): C, 46.80; H, 6.43; N, 9.92; Found (%): C, 46.51; H, 6.65; N, 9.85.

EXAMPLE 2

20 mg of Compound 2 as prepared in Example 1-(6) was dissolved in 2 ml of absolute methanol, and a small amount of metal sodium was added thereto. Three minutes later, disappearance of any unreacted substances was confirmed by thin layer chromatography, and the reaction mixture was treated with Amberlite IR-120 (H+), followed by filtration. From the filtrate was obtained 17.6 mg (yield: 95%) of 2-acetamido-2-deoxy-3-O-(D-2-propanoyl-L-alanyl-D-isoglutamine methyl ester)-1-thio-β-D-glucopyranose (Compound 3) having a melting point of 117°–125° C. (decomposition).

$[\alpha]_D^{25} +24°$ (c=0.2, methanol, equilibrium).

Elemental Analysis for $C_{20}H_{34}N_4O_{10}S$: Calcd. (%): C, 45.97; H, 6.56; N, 10.72; Found (%): C, 45.49, H, 6.53, N, 10.88.

EXAMPLE 3

25 mg of Compound 2 as prepared in Example 1-(6) was dissolved in 2 ml of absolute methanol, and a small amount of metal sodium was added thereto. Three minutes later, 1 ml of 0.2M potassium hydroxide was added to the reaction mixture. After confirming completion of the reaction by thin layer chromatography, the reaction mixture was treated with Amberlite (R-120 (H+)] to remove the base. The solution was concentrated under reduced pressure and freeze-dried from 1,4-dioxane to obtain 22.4 mg (quantitative yield) of 2-acetamido-2-deoxy-3-O-(D-2-propanoyl-L-alanyl-D-isoglutamine)-1-thio-β-D-glucopyranose (Compound 4) having a melting point of 157°–166° C. (decomposition).

$[\alpha]_D^{25} +20°$ (c=0.2, methanol, equilibrium).

Elemental Analysis for $C_{19}H_{32}N_4O_{10}S$: Calcd. (%): C, 44.87; H, 6.34; N, 11.02; Found (%): C, 44.45; H, 6.53; N, 10.99.

EXAMPLE 4

60 mg of Compound 1 as prepared in Example 1-(5) was dissolved in 5 ml of absolute methanol, and 6 mg of sodium methoxide was added thereto. Ninety minutes later, after it was confirmed by thin layer chromatography that the reactant had completely be converted to 2-acetamido-1-S-sodium-2-deoxy-4,6-O-isopropylidene-3-O-(D-2-propanoyl-L-alanyl-D-isogulutamine methyl ester)-1-thio-β-D-glucopyranose (Compound 5), 15 mg of n-butyl bromide was added to the reaction mixture, followed by stirring at room temperature overnight. The reaction mixture was concentrated under reduced pressure, and the resulting syrup was purified by silica gel (10 g) column chromatography (developing agent (a): chloroform; (b): chloroform-methanol=50:1) to obtain 60 mg (yield: 98%) of 1-S-n-butyl 2-acetamido-2-deoxy-4,6-O-isopropylidene-3-O-(D-2-propanoyl-L-alanyl-D-isoglutamine methyl ester)-1-thio-β-D-glucopyranoside (Compound 6) having a melting point of 75°–78° C.

$[\alpha]_D^{25} +25°$ (c=0.5, methanol).

Elemental Analysis for $C_{27}H_{46}N_4O_{10}S$: Calcd. (%): C, 52.41; H, 7.49; N, 9.06; Found (%): C, 52.25; H, 7.45; N, 9.01.

EXAMPLE 5

Compound 5 was prepared in the same manner as in Example 4 but using 83 mg of Compound 1. 43 mg of hexadecanyl bromide was added to the reaction mixture containing Compound 5, and the resulting mixture was stirred at room temperature overnight. The reaction mixture was concentrated under reduced pressure and then purified by silica gel (10 g) column chromatography (developing agent (a): chloroform-methanol=100:1; (b): chloroform-methanol=30:1).

From the effluent (b), there was obtained 100 mg (yield: 93%) of 1-S-hexadecanyl 2-acetamido-2-deoxy-4,6-O-isopropylidene-3-O-(D-2-propanoyl-L-alanyl-D-isoglutamine methyl ester)-1-thio-β-D-glucopyranoside (Compound 7) having a melting point of 93°–96° C.

$[\alpha]_D^{25} +35°$ (c=0.3, chloroform).

Elemental Analysis for $C_{39}H_{70}N_4O_{10}S$: Calcd. (%): C, 59.51; H, 8.97; N, 7.17; Found (%): C, 59.33; H, 8.86; N, 7.15.

EXAMPLE 6

50 mg of Compound 6 as prepared in Example 4 was dissolved in 3 ml of a 8% aqueous acetic acid solution, and hydrolysis was carried out at 45° C. for 60 minutes. After confirming by thin layer chromatography, the reaction mixture was freeze-dried to quantitatively obtain 1-S-n-butyl 2-acetamido-2-deoxy-3-O-(D-2-propanoyl-L-alanyl-D-isoglutamine methyl ester)-1-thio-β-D-glucopyranoside (Compound 8) having a melting point of 155°–160° C. (decomposition).

$[\alpha]_D^{25} +14°$ (c=0.3, methanol).

Elemental Analysis for $C_{24}H_{42}N_4O_{11}S$: Calcd. (%): C, 49.81; H, 7.32; N, 9.68; Found (%): C, 49.45; H, 7.61; N, 9.55.

EXAMPLE 7

50 mg of Compound 7 as prepared in Example 5 was dissolved in 3 ml of a 80% aqueous acetic acid solution and heated at 45° C. for 1 hour. After confirming disappearance of any unreacted substances by thin layer chromatography, the reaction mixture was freeze-dried to obtain 1-S-hexadecanyl 2-acetamido-2-deoxy-3-O-(D-2-propanoyl-L-alanyl-D-isoglutamine methyl ester)-1-thio-β-D-glucopyranoside (Compound 9) having a melting point of 179°–182° C. in a quantitative yield.

$[\alpha]_D^{25} +44°$ (c=0.2, chloroform-methanol=1:1).

Elemental Analysis for $C_{36}H_{66}N_4O_{10}S$: Calcd. (%): C, 57.88; H, 8.91; N, 7.51; Found (%): C, 57.65; H, 8.96; N, 7.43.

EXAMPLE 8

20 mg of Compound 8 as prepared in Example 6 was dissolved in 2 ml of methanol, and 2 ml of 0.2M potassium hydroxide was added thereto. Twenty minutes later, the ester was completely hydrolyzed. The reaction mixture was treated with Amberlite IR-120 (H+), the resulting solution was concentrated under reduced pressure and freeze-dried using 1,4-dioxane to quantitatively obtain 1-S-n-butyl 2-acetamido-2-deoxy-3-O-(D-2-propanoyl-L-alanyl-D-isoglutamine)-1-thio-β-D-glucopyranoside (Compound 10) having a melting point of 108°–112° C. (decomposition).

$[\alpha]_D^{25} -15°$ (c=0.3, methanol).

Elemental Analysis for $C_{23}H_{40}N_4O_{11}S$: Calcd. (%): C, 48.92; H, 7.14; N, 9.92; Found (%): C, 48.65; H, 7.49; N, 9.65.

EXAMPLE 9

17 mg of Compound 9 as prepared in Example 7 was dissolved in a mixture of 3 ml of 1,4-dioxane and 1 ml of methanol, and 2 ml of 0.2M potassium hydroxide was added thereto. Twenty minutes later, the methyl ester was completely hydrolyzed. The reaction mixture was treated with Amberlite IR-120 (H+), the resulting solution was concentrated and freeze-dried from dioxane to quantitatively give 1-S-hexadecanyl 2-acetamido-2-deoxy-3-O-(D-2-propanoyl-L-alanyl-D-isoglutamine)-

1-thio-β-D-glucopyranoside (Compound 11) having a melting point of 110°–115° C. (decomposition).

$[\alpha]_D^{25} +24°$ (c=0.15, methanol).

Elemental Analysis for $C_{35}H_{64}N_4O_{10}S$: Calcd. (%): C, 57.35; H, 8.80; N, 7.64; Found (%): C, 57.09; H, 8.95; N, 7.55.

EXAMPLE 10

85 mg of Compound 1 as prepared in Example 1-(5) was dissolved in 5 ml of absolute methanol, and 10 mg of sodium methoxide was added thereto. After 1.5 hours, the reaction mixture was treated with Amberlite IRC-50 (H+) and then concentrated. The resulting syrup was purified by silica gel (10 g) column chromatography (developing agent (a): chloroform; (b): chloroform-methanol=40:1). From the effluent (b) was obtained 76 mg (yield: 96%) of 2-acetamido-2-deoxy-4,6-O-isopropylidene-3-O-(D-2-propanoyl-L-alanyl-D-isoglutamine methyl ester)-1-thio-β-D-glucopyranose (Compound 12). Recrystallization from diethyl ether gave a product having a melting point of 105°–107° C. (decomposition).

$[\alpha]_D^{25} +33°$ (c=0.5, chloroform).

Elemental Analysis for $C_{23}H_{38}N_4O_{10}S$: Calcd. (%): C, 49.10; H, 6.81; N, 9.96; Found (%): C, 49.21; H, 6.77; N, 9.83.

EXAMPLE 11

60 mg of Compound 12 as prepared in Example 10 was dissolved in a mixture of 2 ml of anhydrous dichloromethane and 1 ml of pyridine, and 1 ml of dichloromethane containing 40 mg of hexadecanoyl chloride was added thereto under cooling. The reaction completed in 1 hour. To the reaction mixture was added 1 ml of methanol, and the mixture was concentrated under reduced pressure. The resulting syrup was extracted with chloroform, washed with water and dried over sodium sulfate. The chloroform was distilled off, and the residue was purified by silica gel (10 g) column chromatography (developing agent (a): chloroform-methanol=100:1; (b): chloroform-methanol=50:1; (c): chloroform-methanol=30:1). From the effluent (c), there was obtained 70 mg (yield: 82%) of 2-acetamido-2-deoxy-1-S-hexadecanoyl-4,6-O-isopropylidene-3-O-(D-2-propanoyl-L-alanyl-D-isoglutamine methyl ester)-1-thio-β-D-glucopyranose (Compound 13) having a melting point of 98°–100° C.

$[\alpha]_D^{25} +30°$ (c=0.2, chloroform).

Elemental Analysis for $C_{39}H_{68}N_4O_{11}S$: Calcd. (%): C, 58.47; H, 8.56; N, 6.99; Found (%): C, 58.53; H, 8.63; N, 6.75.

EXAMPLE 12

50 mg of Compound 13 as prepared in Example 11 was dissolved in 3 ml of a 80% aqueous acetic acid solution and heated at 45° C. for 1 hour to hydrolyze the isopropylidene group. The reaction mixture was concentrated under reduced pressure and crystallized from diethyl ether to give 43 mg (yield: 91%) of 2-acetamido-2-deoxy-1-S-hexadecanoyl-3-O-(D-2-propanoyl-L-alanyl-D-isoglutamine methyl ester)-1-thio-β-D-glucopyranose (Compound 14) having a melting point of 181°–183° C. which showed a single spot on thin layer chromatography.

$[\alpha]_D^{25} +63°$ (c=0.2, chloroform-methanol=1:1).

Elemental Analysis for $C_{36}H_{64}N_4O_{11}S$: Calcd. (%): C, 56.82; H, 8.48; N, 7.36; Found (%): C, 56.77; H, 8.56; N, 7.35.

EXAMPLE 13

80 mg of Compound 1 as prepared in Example 1-(5) was dissolved in 5 ml of absolute methanol, and 10 mg of sodium methoxide was added thereto. After the mixture was allowed to stand at room temperature for 1 hour, 5 ml of 0.2M potassium hydroxide was added thereto. Five minutes later, the base was removed by treating with Amberlite IRC-50 (H+) resin, and the resin was washed with methanol. The filtrate and the washing were combined and concentrated under reduced pressure at a temperature below 40° C. to obtain 2-acetamido-2-deoxy-4,6-O-isopropylidene-3-O-(D-2-propanoyl-L-alanyl-D-isoglutamine)-1-thio-β-D-glucopyranose (Compound 15). The product was dissolved in a mixture of 2 ml of anhydrous dichloromethane and 1 ml of pyridine, and to the resulting solution was added a solution of 45 mg of hexadecanoyl chloride in 1 ml of anhydrous dichloromethane under ice-cooling, followed by stirring for 1.5 hours. The excess of the chloride was decomposed with methanol, and the decomposition solution was concentrated under reduced pressure. The residue was extracted with chloroform, washed with water and dried over sodium sulfate. The chloroform was distilled off, and the resulting syrup was purified by silica gel (20 g) column chromatography (developing agent (a): chloroform-methanol=50:1; (b) chloroform-methanol=10:1). From the effluent (b), there was obtained 75 mg (yield: 72%) of 2-acetamido-2-deoxy-1-S-hexadecanoyl-4,6-O-isopropylidene-3-O-(D-2-propanoyl-L-alanyl-D-isoglutamine)-1-thio-β-D-glucopyranose (Compound 16) having a melting point of 103°–106° C.

$[\alpha]_D^{25} +42°$ (c=0.15, chloroform-methanol=1:1).

Elemental Analysis for $C_{38}H_{66}N_4O_{11}S$: Calcd. (%): C, 57.99; H, 8.45; N, 7.12; Found (%): C, 57.65; H, 8.69; N, 7.05.

EXAMPLE 14

30 mg of Compound 16 as prepared in Example 13 was dissolved in 2 ml of a 80% aqueous acetic acid solution and heated at 45° C. for 1 hour to completely hydrolyze the isopropylidene group. After confirming that the thin layer chromatography showed a single spot, the reaction mixture was freeze-dried to obtain 28 mg of 2-acetamido-2-deoxy-1-S-hexadecanoyl-3-O-(D-2-propanoyl-L-alanyl-D-isoglutamine)-1-thio-β-D-glucopyranose (Compound 17) as a colorless amorphous substance having a melting point of 125°–129° C.

$[\alpha]_D^{25} +62.5°$ (c=0.2, chloroform-methanol=1:1).

Elemental Analysis for $C_{35}H_{62}N_4O_{11}S$: Calcd. (%): C, 56.28; H, 8.73; N, 7.50; Found (%): C, 55.95, H, 8.51; N, 7.46.

EXAMPLE 15

To a solution of 85 mg of Compound 1 in 5 ml of methanol was added 10 mg of sodium methoxide and the mixture was kept for 1.5 hours at room temperature, and treated with Amberlite IRC-50 (H+) resin to remove the base. The mixture was concentrated and the residue was chromatographed on a column of silica gel (10 g) with chloroform and 40:1 chloroform-methanol. The latter eluate gave 76 mg of 2-acetamido-2-deoxy-4,6-O-isopropylidene-3-O-(D-2-propanoyl-L-alanyl-D-isoglutamine methyl ester)-1-thio-β-D-glucopyranose as crystals having a melting point of 105°–107° C. (decomposition).

$[\alpha]_D^{25} -33°$ (c=0.5, chloroform).

Elemental Analysis for $C_{23}H_{38}N_4O_{10}S$: Calcd. (%): C, 49.10; H, 6.81; N, 9.96; Found (%): C, 48.89; H, 6.85; N, 9.83.

To an ice-cooled solution of 80 mg of the above compound in 1 ml of dry pyridine and 2 ml of dichloromethane was dropwise added, with stirring, a solution of 52 mg of decanoyl chloride in 1 ml of dichloromethane, and the mixture was stirred for 40 minutes at 5° to 10°. 0.5 ml of methanol was added to the mixture and the resulting mixture was concentrated and then extracted with chloroform. The extract was washed with water, dried over sodium sulfate and concentrated to a syrup which was then chromatographed on a column of silica gel (15 g) with (a) 150:1, (b) 70:1, and (c) 30:1 chloroform-methanol. Eluant (a) gave 65 mg of amorphous 2-acetamido-2-deoxy-1-S-decanoyl-4,6-O-isopropylidene-3-O-(D-2-propanoyl-L-alanyl-D-isoglutamine methyl ester)-1-thio-β-D-glucopyranose.

$[\alpha]_D^{25} + 6.6°$ (c=0.33, chloroform).

Elemental Analysis for $C_{33}H_{56}N_4O_{11}S_4$

A solution of 50 mg of the above compound in 2 ml of 80% aqueous acetic acid was heated for 2 hours at 45° C. and the mixture was concentrated to give a crystalline mass. Recrystallization from ether gave 2-acetamido-2-deoxy-1-S-decanoyl-3-O-(D-2-propanoyl-L-alanyl-D-isoglutamine methyl ester)-1-thio-β-D-glucopyranose (Compound 18) having a melting point of 176.5°.

$[\alpha]_D^{25} + 41.3°$ (c=0.44, 1:1 chloroform-methanol).

Elemental Analysis for $C_{30}H_{52}N_4O_{11}S$: Calcd. (%): C, 53.23; H, 7.74; N, 8.28; Found (%): C, 53.31; H, 7.89; N, 8.33.

EXAMPLES 16 AND 17

The following compounds were prepared in the same manner as above.

2-Acetamido-2-deoxy-1-S-octadecanoyl-3-O-(D-2-propanoyl-L-alanyl-D-isoglutamine methyl ester)-1-thio-β-D-glucopyranose (Compound 19) as an amorphous substance.

$[\alpha]_D^{25} + 29.0°$ (c=0.64, 1:1 chloroform-methanol).

Elemental Analysis for $C_{38}H_{68}N_4O_{11}S$: Calcd. (%): C, 57.84; H, 8.69; N, 7.10; Found (%): C, 57.55; H, 8.73; N, 7.01.

2-Acetamido-2-deoxy-1-S-triacontanoyl-3-O-(D-2-propanoyl-L-alanyl-D-isoglutamine methyl ester)-1-thio-β-D-glucopyranose (Compound 20).

m.p. 182°, $[\alpha]_D^{25} + 33.3°$ (c=0.6, 1:1 chloroform-methanol).

Elemental Analysis for $C_{50}H_{92}N_4O_{11}S$: Calcd. (%): C, 62.73; H, 9.69; N, 5.85; Found (%): C, 62.65; H, 9.83; N, 5.81.

While the invention has been described in detail and with reference to specific embodiments thereof, it will be apparent to one skilled in the art that various changes and modifications can be made therein without departing from the spirit and scope thereof.

What is claimed is:

1. A muramyldipeptide derivative represented by the formula:

$$\begin{array}{c} R_1O-CH_2 \\ \diagup O \\ \phantom{xx} SR_3 \\ R_2O \\ \phantom{xxx} NH-Acyl \\ CH_3CHCO-Ala-NH-CHCH_2CH_2COOR_4 \\ \phantom{xxxxxxxxxxxxxxxxxxxxxxx} | \\ \phantom{xxxxxxxxxxxxxxxxxxxxxxx} CONH_2 \end{array}$$

wherein Ala represents alanine; Acyl represents an acyl group having 2 to 40 carbon atoms; $R_1$ and $R_2$ each represents a hydrogen atom or, when taken together, may form an alkylidene group having 1 to 6 carbon atoms; $R_3$ represents an acyl group having 2 to 40 carbon atoms; and $R_4$ represents a hydrogen atom or an alkyl group having 1 to 20 carbon atoms.

2. The compound as claimed in claim 1, wherein $R_1$ and $R_2$ each represents a hydrogen atom; $R_3$ represents an acyl group having 2 to 40 carbon atoms; and $R_4$ represents an alkyl group having 1 to 20 carbon atoms.

3. The compound as claimed in claim 1, wherein said compound is 2-acetamido-2-deoxy-1-S-decanoyl-3-O-(D-glucopyranose.

4. The compound as claimed in claim 1, wherein said compound is 2-acetamido-1-S-acetyl-2-deoxy-3-O-(D-2-propanoyl-L-alanyl-D-isoglutamine methyl ester)-1-thio-β-D-glucopyranose.

5. The compound as claimed in claim 1, wherein said compound is 2-acetamido-2-deoxy-3-O-(D-2-propanoyl-L-alanyl-D-isoglutamine methyl ester)-1-thio-β-D-glucopyranose.

6. The compound as claimed in claim 1, wherein said compound is 2-acetamido-2-deoxy-3-O-(D-2-propanoyl-L-alanyl-D-isoglutamine)-1-thio-β-D-glucopyranose.

7. The compound as claimed in claim 1, wherein said compound is 2-acetamido-2-deoxy-1-S-hexadecanoyl-3-O-(D-2-propanoyl-L-alanyl-D-isoglutamine methyl ester)-1-thio-β-D-glucopyranose.

8. The compound as claimed in claim 1, wherein said compound is 2-acetamido-2-deoxy-1-S-hexadecanoyl-3-O-(D-2-propanoyl-L-alanyl-D-isoglutamine)-1-thio-β-D-glucopyranose.

9. The compound as claimed in claim 1, wherein said compound is 2-acetamido-2-deoxy-1-S-eicosanoyl-3-O-(D-2-propanoyl-L-alanyl-D-isoglutamine)-1-thio-β-D-glucopyranose.

* * * * *